United States Patent
Różański et al.

(10) Patent No.: US 9,169,267 B2
(45) Date of Patent: Oct. 27, 2015

(54) QUATERNARY AMMONIUM SALTS, METHOD FOR PREPARATION AND APPLICATIONS THEREOF

(71) Applicants: Jakub Różański, Poznań (PL); Agnieszka Gielara-Korzańska, Tulce (PL); Stanislaw Sobiak, Poznań (PL); Marcelina Maria Kubicka, Gniezno (PL); Helena Kukuła, Skórzewo (PL)

(72) Inventors: Jakub Różański, Poznań (PL); Agnieszka Gielara-Korzańska, Tulce (PL); Stanislaw Sobiak, Poznań (PL); Marcelina Maria Kubicka, Gniezno (PL); Helena Kukuła, Skórzewo (PL)

(73) Assignee: Uniwersytet Medyczny IM. Karola Marcinkowskiego, Poznan (PL)

( * ) Notice: Subject to any disclaimer, the term of this patent is extended or adjusted under 35 U.S.C. 154(b) by 0 days.

(21) Appl. No.: 14/375,363

(22) PCT Filed: Jan. 31, 2013

(86) PCT No.: PCT/PL2013/000010
§ 371 (c)(1),
(2) Date: Jul. 29, 2014

(87) PCT Pub. No.: WO2013/115661
PCT Pub. Date: Aug. 8, 2013

(65) Prior Publication Data
US 2015/0080583 A1    Mar. 19, 2015

(30) Foreign Application Priority Data

Jan. 31, 2012  (PL) .......................................... 397951

(51) Int. Cl.
*C07D 498/04* (2006.01)

(52) U.S. Cl.
CPC ................................... *C07D 498/04* (2013.01)

(58) Field of Classification Search
CPC ..................................................... C07D 498/04
See application file for complete search history.

(56) References Cited

PUBLICATIONS

European U.S. Pat. No. 0 504 936 A1, (Nippon Paint Co Ltd [JP]); published Sep. 23, 1992.
German Patent No. DE 17 70 781 A1, (Huels Chemische Werke AG); published Jan. 13, 1972.
International Search Report issued by the International Searching Authority (ISA/O.E.P.M.) on May 21, 2103 in connection with International Application No. PCT/PL2013/000010.
Written Opinion of the International Searching Authority for PCT/PL2013/000010, dated Jul. 31, 2014.
International Preliminary Report on Patentability for PCT/PL2013/000010, dated Aug. 5, 2014.

*Primary Examiner* — Samantha Shterengarts
(74) *Attorney, Agent, or Firm* — Gary J. Gershik; Cooper & Dunham LLP

(57) ABSTRACT

The invention relates to a novel class of quaternary ammonium salts containing tetra-hydro[1,3]oxazolo[2,3-b][1,3]oxazol-4-ium moiety in the structure, in particular the new derivatives of 4-methyltetrahydro[1,3]oxazolo[2,3-b][1,3]oxazol-4-ium, 4-(2-oxoethyl)tetrahydro[1,3]oxazolo[2,3-6][1,3]oxazol-4-ium, bis{4-methyltetrahydro[1,3]oxazoio[2,3-6][1,3]oxazol-4-ium}, bis{4-(2-oxoethyl)tetrahydro[1,3]oxazolo[2,3-b][1,3]oxazol-4-ium} and tris{4-methyltetrahydro[1,3]oxazolo[2,3-b][1,3]oxazol-4-ium} salts, process for the preparation of a novel class of quaternary ammonium salts and applications thereof.

20 Claims, 1 Drawing Sheet

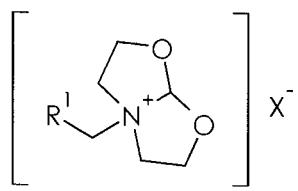
structure 1
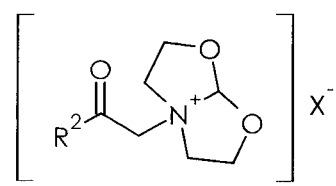
structure 2
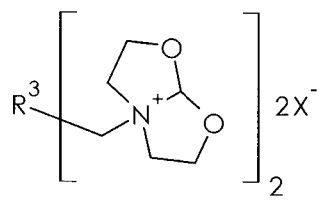
structure 3
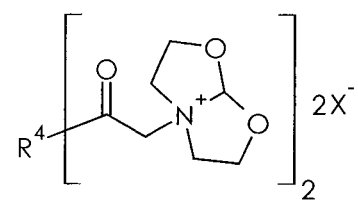
structure 4
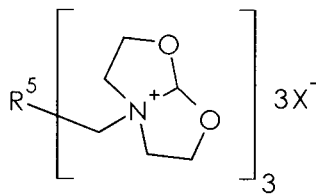
structure 5

QUATERNARY AMMONIUM SALTS, METHOD FOR PREPARATION AND APPLICATIONS THEREOF

This application is a §371 national stage of PCT International Application No. PCT/PL2013/000010, filed Jan. 31, 2013, designating the United States and claiming priority of Polish Application No. P.397951, filed Jan. 31, 2012, the contents of all of which are hereby incorporated by reference into this application.

The present invention relates to a novel class of quaternary ammonium salts containing tetrahydro[1,3]oxazolo[2,3-b][1,3]oxazol-4-ium moiety in the structure, process for the preparation of a novel class of quaternary ammonium salts and applications thereof.

Quaternary ammonium salts (QAS) are chemical compounds of the molecular formula $[R^1R^2R^3R^4]N^+X^-$, wherein X represents mononegative ion, usually halide, and $R^1$-$R^4$ are carbon chains with different length and structure, usually substituted with further functional groups. In some ammonium salts nitrogen atom is a part of five-, six- or seven-membered aromatic or non-aromatic ring. Due to amphiphilic character, quaternary ammonium salts are cationic surfactants having a broad spectrum of practical applications in many branches of modern economy. In the cosmetic industry, QAS are used as a cleaning agents, antistatics, foam-makers, emulsifiers, softeners, moisturizers or stabilisers used for the production of detergents, creams, shampoos, balms, shaving foams, hair dyes and regenerating conditioners. Because of their anticorrosive and antistatic effect on such textiles as wool, cotton, synthetic and cellulose fibres, liquids with QAS are used for rinsing and softening of textiles. The surfactant activity of quaternary ammonium salts facilitates the penetration of chemical substances through biological membranes. Pharmaceutical companies use this property for production of modern forms of drugs, such as emulsions, ointments, gels, capsules, suppositories, etc. Ammonium salts exhibit very strong activity against bacteria, fungi, protozoans and some viruses, therefore, they are commonly applied as disinfectants, antiseptics and preservatives. In agriculture and wood industry they are applied as active components of preparations protecting wood or plants from diseases caused by fungi and other microorganisms.

In anaesthesiology the quaternary ammonium salts are used as skeletal muscle relaxants with depolarising or non-depolarising mechanism of action.

These compounds are also helpful in the technology of production and processing of unsaturated polyester resins, which are used for the production of laminates for manufacturing boats, yachts, aeroplanes, gliders, shower cabins, bathtubs, etc. QAS are also used in scientific research laboratories and industrial technological installations as phase transfer catalysts (PTC). Such compounds enable transfer of individual reagents from one thermodynamic phase to another, which is of particular importance to the course of reaction when it takes place in an environment with more than one thermodynamic phase and one or more reagents are soluble in one phase but insoluble in the other. Finally, as ionic liquids QAS are more and more often applied in chemical production processes, where they replace traditional toxic solvents.

In its first aspect, the present invention provides a novel class of quaternary ammonium salts containing tetrahydro[1,3]oxazolo[2,3-b][1,3]oxazol-4-ium moiety, in particular the new derivatives of 4-methyltetrahydro[1,3]oxazolo[2,3-b][1,3]oxazol-4-ium, 4-(2-oxoethyl)tetrahydro[1,3]oxazolo[2,3-b][1,3]oxazol-4-ium, bis{4-methyltetrahydro[1,3]oxazolo[2,3-b][1,3]oxazol-4-ium}, bis{4-(2-oxoethyl)tetrahydro[1,3]oxazolo[2,3-b][1,3]oxazol-4-ium} and tris{4-methyltetrahydro[1,3]oxazolo[2,3-b][1,3]oxazol-4-ium} salts.

According to the first aspect, the invention relates to the new 4-methyltetrahydro[1,3]oxazolo[2,3-b][1,3]oxazol-4-ium derivatives of general formula (1),

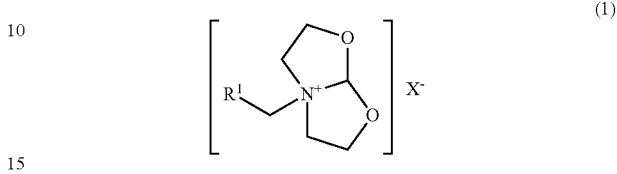

(1)

wherein:
$R^1$ is phenyl; 2-nitrophenyl; 3-nitrophenyl; 4-nitrophenyl; 2-bromophenyl; 3-bromophenyl; 4-bromophenyl; 2,3-dibromophenyl; 2,4-dibromophenyl; 2-chlorophenyl; 3-chlorophenyl; 4-chlorophenyl; 2,4-dichlorophenyl; 3,4-dichlorophenyl; 3,5-dichlorophenyl; 2,6-dichlorophenyl; 2-iodophenyl; 4-iodophenyl; 2-methoxyphenyl; 3-methoxyphenyl; 4-methoxyphenyl; 2,5-dimethoxyphenyl; 3,4-dimethoxyphenyl; 2,3,4-trimethoxyphenyl; 3,4,5-trimethoxyphenyl; 2-methylphenyl; 3-methylphenyl; 4-methylphenyl; 3,5-dimethylphenyl; 2,4-dimethylphenyl; 2-fluorophenyl; 3-fluorophenyl; 4-fluorophenyl; 3,4-difluorophenyl; 2,3-difluorophenyl; 3,5-difluorophenyl; 2,4-difluorophenyl; 2,3,4,5-tetrafluorophenyl; 2-(methoxycarbonyl)phenyl; 3-(methoxycarbonylphenyl; 4-(methoxycarbonyl)phenyl; 2-(trifluoromethyl)phenyl; 3-(trifluoromethyl)phenyl; 4-(trifluoromethyl)phenyl; 4-tert-butylphenyl; 2-phenylophenyl; 3-phenylophenyl; 4-phenylophenyl; 4-benzoylphenyl; 4-benzyloxyphenyl; 4-(methylsulphonyl)phenyl; 2-cyanophenyl; 3-cyanophenyl; 4-cyanophenyl; 4-formylphenyl; 4-methylthiophenyl; 3-phenoxyphenyl; 4-phenoxyphenyl; 2,4-diphenoxyphenyl; 2,4-dinitrophenyl; 4-(aminosulfonyl)phenyl; 2-pyridyl; 3-pyridyl; 4-pyridyl; 2-furyl; 2-thienyl; 2-benzo[b]furyl; 1-naphthyl or 2-naphthyl;

X is chloride, bromide or iodide.

According to the first aspect, the invention also relates to the new 4-(2-oxoethyl)tetrahydro[1,3]oxazolo[2,3-b][1,3]oxazol-4-ium derivatives of general formula (2),

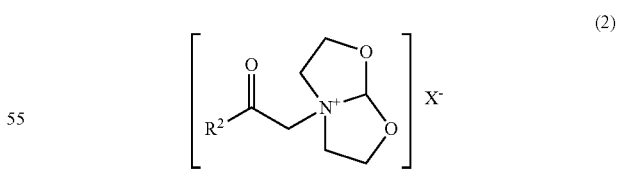

(2)

wherein:
$R^2$ is phenyl; 2-fluorophenyl; 3-fluorophenyl; 4-fluorophenyl; 2,4-difluorophenyl; 2,5-difluorophenyl; 2,6-difluorophenyl; 2,3,4-trichlorophenyl; 2,3,4,5-tetrafluorophenyl; 2-chlorophenyl; 3-chlorophenyl; 4-chlorophenyl; 2,4-dichlorophenyl; 3,4-dichlorophenyl; 2,5-dichlorophenyl; 2-bromophenyl; 3-bromophenyl; 4-bromophenyl; 3-iodophenyl; 4-iodophenyl; 2-hydroxyphenyl; 3-hydroxyphenyl; 4-hydroxyphenyl; 2,4-dihydroxyphenyl; 2,3-dihydroxyphenyl; 3,4-dihydroxyphenyl; 2,5-dihydroxyphenyl; 2-(acetyloxy)phenyl; 3-(acetyloxy)phenyl; 4-(acetyloxy)phenyl; 2,4-bis(acetyloxy)phenyl; 3,4-bis(acetyloxy)phenyl; 2,5-bis(acetyloxy)phenyl; 1,3-benzodioxol-5-yl; 2-phenylophenyl; 3-phenylophenyl; 4-phenylophenyl; 2-nitrophenyl; 3-nitrophenyl; 4-nitrophenyl; 2,4-dinitrophenyl; 3,4-dinitrophenyl; 2,5-dinitrophenyl; 4-chloro-3-nitrophenyl; 2-chloro-3-nitrophenyl; 2-methylphenyl; 3-methylphenyl; 4-methylphenyl; 2,4-dimethylphenyl; 3,4-dimethylphenyl; 2-methoxyphenyl; 3-methoxyphenyl; 4-methoxyphenyl; 3,4-dimethoxyphenyl; 2,4-dimethoxyphenyl; 2,5-dimethoxyphenyl; 3,4,5-trimethoxyphenyl; 4-ethylphenyl; 3-benzyloxyphenyl; 4-benzyloxyphenyl; 4-phenoxyphenyl; 2-cyanophenyl; 3-cyanophenyl; 4-cyanophenyl; 2-aminophenyl; 3-aminophenyl; 4-aminophenyl; 3-(trifluoromethyl)phenyl; 4-(trifluoromethyl)phenyl; 4-carbamoylphenyl; 4-sulfamoylphenyl; 4-(methylsulfonyl)phenyl; 4-(methoxycarbonyl)phenyl; 4-(acetylamino)phenyl; 4-(N,N-dimethylamino)phenyl; 4-tert-butylphenyl; trifluoromethyl; trichloromethyl; 2-pyridyl; 3-pyridyl; 4-pyridyl; 1-naphthyl; 2-naphthyl; 2-furyl; 2-benzo[b]furyl; 2-thienyl; amino; methylamino; dimethylamino; phenylamino; diphenylamino; benzylamino or dibenzylamino;

X is chloride, bromide or iodide.

According to the first aspect, the invention also relates to the new bis{4-methyltetrahydro[1,3]oxazolo[2,3-b][1,3]oxazol-4-ium} derivatives of general formula (3),

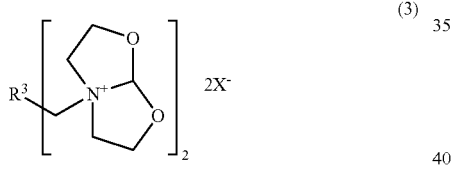

(3)

wherein:

$R^3$ is benzene-1,4-diyl; benzene-1,3-diyl; 1,2-dioxoethan-1,2-diyl; biphenyl-4,4'-diyl; methanediyldibenzene-4,1-diyl; oxodibenzene-4,1-diyl or carbonyldibenzene-4,1-diyl;

X is chloride, bromide or iodide.

According to the first aspect, the invention also relates to the new bis{4-(2-oxoethyl)tetrahydro[1,3]oxazolo[2,3-b][1,3]oxazol-4-ium} derivatives of general formula (4),

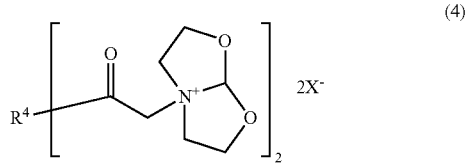

(4)

wherein:

$R^4$ is benzene-1,4-diyl; benzene-1,3-diyl; biphenyl-4,4'-diyl or oxydibenzene-4,1-diyl;

X is chloride, bromide or iodide.

According to the first aspect, the invention also relates to the new tris{4-methyltetrahydro[1,3]oxazolo[2,3-b][1,3]oxazol-4-ium} derivatives of general formula (5),

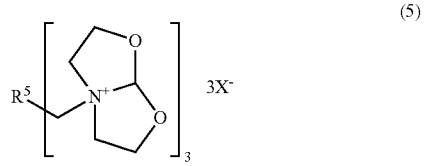

(5)

wherein:

$R^5$ is benzene-1,3,5-triyl;

X is chloride, bromide or iodide.

In a further aspect of the invention, a process for the preparation of the novel class of quaternary ammonium salts containing tetrahydro[1,3]oxazolo[2,3-b][1,3]oxazol-4-ium moiety is provided. In particular, the invention relates to the preparation of the new derivatives of general formula (1) or (2) or (3) or (4) or (5), wherein:

$R^1$ or $R^3$ or $R^5$ is non-substituted or substituted group selected from alkyl, cycloalkyl, aryl or heteroaryl, wherein substituted group denotes group substituted with radical independently selected from alkyl, aryl, acyl, alkoxyl, aryloxyl, alkoxycarbonyl, aryloxycarbonyl, halogen, cyano, alkylthio, arylthio, alkylsulfonyl, arylsulfonyl, aminosulfonyl, nitro, amino, mono- or dialkylamino, mono- or diarylamino or acylamino;

$R^2$ or $R^4$ is non-substituted or substituted group selected from alkyl, cycloalkyl, aryl, heteroaryl, amino, mono- or dialkylamino, mono- or diarylamino or acylamino, wherein substituted group denotes group substituted with radical independently selected from alkyl, aryl, acyl, alkoxyl, aryloxyl, alkoxycarbonyl, aryloxycarbonyl, halogen, cyano, alkylthio, arylthio, alkylsulfonyl, arylsulfonyl, aminosulfonyl, nitro, amino, mono- or dialkylamino, mono- or diarylamino or acylamino;

X is fluoride, chloride, bromide, iodide or methanesulfonate.

The Process for preparation of the 4-methyltetrahydro[1,3]oxazolo[2,3-b][1,3]oxazol-4-ium derivatives of general formula (1) is shown in scheme 1.

scheme 1

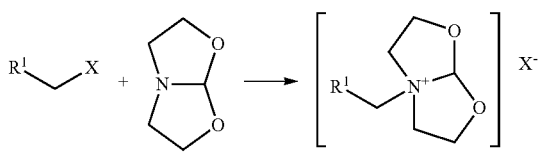

It comprises the reaction of a compound of general formula (6),

(6)

with a bicyclic amide acetal known as tetrahydro[1,3]oxazolo[2,3-b][1,3]oxazole or 1-aza-4,6-dioxabicyclo[3.3.0]octane of formula (7),

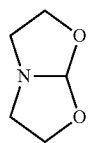

(7)

wherein R¹ and X have the above-mentioned meaning.

Preferably R¹ is phenyl; 2-nitrophenyl; 3-nitrophenyl; 4-nitrophenyl; 2-bromophenyl; 3-bromophenyl; 4-bromophenyl; 2,3-dibromophenyl; 2,4-dibromophenyl; 2-chlorophenyl; 3-chlorophenyl; 4-chlorophenyl; 2,4-dichlorophenyl; 3,4-dichlorophenyl; 3,5-dichlorophenyl; 2,6-dichlorophenyl; 2-iodophenyl; 4-iodophenyl; 2-methoxyphenyl; 3-methoxyphenyl; 4-methoxyphenyl; 2,5-dimethoxyphenyl; 3,4-dimethoxyphenyl; 2,3,4-trimethoxyphenyl; 3,4,5-trimethoxyphenyl; 2-methylphenyl; 3-methylphenyl; 4-methylphenyl; 3,5-dimethylphenyl; 2,4-dimethylphenyl; 2-fluorophenyl; 3-fluorophenyl; 4-fluorophenyl; 3,4-difluorophenyl; 2,3-difluorophenyl; 3,5-difluorophenyl; 2,4-difluorophenyl; 2,3,4,5-tetrafluorophenyl; 2-(methoxycarbonyl)phenyl; 3-(methoxycarbonyl)phenyl; 4-(methoxycarbonyl)phenyl; 2-(trifluoromethyl)phenyl; 3-(trifluoromethyl)phenyl; 4-(trifluoromethyl)phenyl; 4-tert-butylphenyl; 2-phenylophenyl; 3-phenylophenyl; 4-phenylophenyl; 4-benzoylphenyl; 4-benzyloxyphenyl; 4-(methylsulphonyl)phenyl; 2-cyanophenyl; 3-cyanophenyl; 4-cyanophenyl; 4-formylphenyl; 4-methylthiophenyl; 3-phenoxyphenyl; 4-phenoxyphenyl; 2,4-diphenoxyphenyl; 2,4-dinitrophenyl; 4-(aminosulfonyl)phenyl; 2-pyridyl; 3-pyridyl; 4-pyridyl; 2-furyl; 2-thienyl; 2-benzo[b]furyl; 1-naphthyl or 2-naphthyl; and X is chloride, bromide or iodide.

It is also preferable to carry out the reaction between approximately equimolar amounts of both reactants.

The Process for preparation of the 4-(2-oxoethyl)tetrahydro[1,3]oxazolo[2,3-b][1,3]oxazol-4-ium derivatives of general formula (2) is shown in scheme 2.

scheme 2

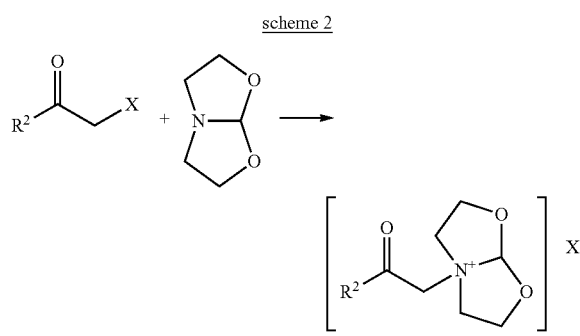

It comprises the reaction of a compound of general formula (8),

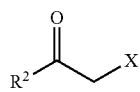

(8)

with tetrahydro[1,3]oxazolo[2,3-b][1,3]oxazole of formula (7), wherein R² has the above-mentioned meaning and X is fluoride, chloride, bromide, iodide or methanesulfonate.

Preferably R² is phenyl; 2-fluorophenyl; 3-fluorophenyl; 4-fluorophenyl; 2,4-difluorophenyl; 2,5-difluorophenyl; 2,6-difluorophenyl; 2,3,4-trichlorophenyl; 2,3,4,5-tetrafluorophenyl; 2-chlorophenyl; 3-chlorophenyl; 4-chlorophenyl; 2,4-dichlorophenyl; 3,4-dichlorophenyl; 2,5-dichlorophenyl; 2-bromophenyl; 3-bromophenyl; 4-bromophenyl; 3-iodophenyl; 4-iodophenyl; 2-hydroxyphenyl; 3-hydroxyphenyl; 4-hydroxyphenyl; 2,4-dihydroxyphenyl; 2,3-dihydroxyphenyl; 3,4-dihydroxyphenyl; 2,5-dihydroxyphenyl; 2-(acetyloxy)phenyl; 3-(acetyloxy)phenyl; 4-(acetyloxy)phenyl; 2,4-bis(acetyloxy)phenyl; 3,4-bis(acetyloxy)phenyl; 2,5-bis(acetyloxy)phenyl; 1,3-benzodioxol-5-yl; 2-phenylophenyl; 3-phenylophenyl; 4-phenylophenyl; 2-nitrophenyl; 3-nitrophenyl; 4-nitrophenyl; 2,4-dinitrophenyl; 3,4-dinitrophenyl; 2,5-dinitrophenyl; 4-chloro-3-nitrophenyl; 2-chloro-3-nitrophenyl; 2-methylphenyl; 3-methylphenyl; 4-methylphenyl; 2,4-dimethylphenyl; 3,4-dimethylphenyl; 2-methoxyphenyl; 3-methoxyphenyl; 4-methoxyphenyl; 3,4-dimethoxyphenyl; 2,4-dimethoxyphenyl; 2,5-dimethoxyphenyl; 3,4,5-trimethoxyphenyl; 4-ethylphenyl; 3-benzyloxyphenyl; 4-benzyloxyphenyl; 4-phenoxyphenyl; 2-cyanophenyl; 3-cyanophenyl; 4-cyanophenyl; 2-aminophenyl; 3-aminophenyl; 4-aminophenyl; 3-(trifluoromethyl)phenyl; 4-(trifluoromethyl)phenyl; 4-carbamoylphenyl; 4-sulfamoylphenyl; 4-(methylsulfonyl)phenyl; 4-(methoxycarbonyl)phenyl; 4-(acetylamino)phenyl; 4-(N,N-dimethylamino)phenyl; 4-tert-butylphenyl; trifluoromethyl; trichloromethyl; 2-pyridyl; 3-pyridyl; 4-pyridyl; 1-naphthyl; 2-naphthyl; 2-furyl; 2-benzo[b]furyl; 2-thienyl; amino; methylamino; dimethylamino; phenylamino; diphenylamino; benzylamino or dibenzylamino; and X is chloride, bromide or iodide.

It is also preferable to carry out the reaction between approximately equimolar amounts of both reactants.

The Process for preparation of the bis{4-methyltetrahydro[1,3]oxazolo[2,3-b][1,3]oxazol-4-ium} derivatives of general formula (3) is shown in scheme 3.

scheme 3

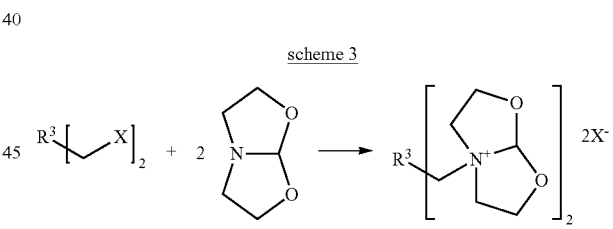

It comprises the reaction of a compound of general formula (9), (9)

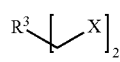

with tetrahydro[1,3]oxazolo[2,3-b][1,3]oxazole of formula (7), wherein R³ has the above-mentioned meaning and X is fluoride, chloride, bromide, iodide or methanesulfonate.

Preferably R³ is benzene-1,4-diyl; benzene-1,3-diyl; 1,2-dioxoethan-1,2-diyl; biphenyl-4,4'-diyl; methanediyldibenzene-4,1-diyl; oxodibenzene-4,1-diyl or carbonyldibenzene-4,1-diyl; and X is chloride, bromide or iodide.

It is also preferable using in the reaction approximately double molar amount of tetrahydro[1,3]oxazolo[2,3-b][1,3]oxazole of formula (7).

The Process for preparation of the new bis{4-(2-oxoethyl) tetrahydro[1,3]oxazolo[2,3-b][1,3]-oxazol-4-ium} derivatives of general formula (4) is shown in scheme 4.

scheme 4

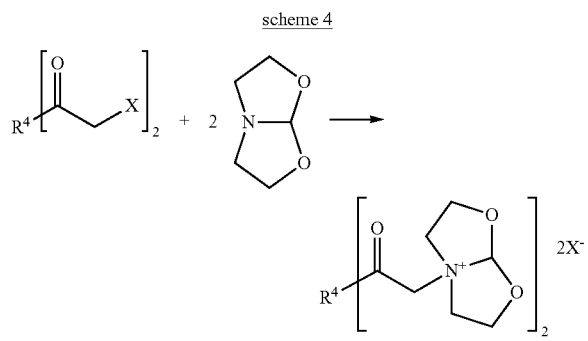

It comprises the reaction of a compound of general formula (10), (10)

with tetrahydro[1,3]oxazolo[2,3-b][1,3]oxazole of formula (7), wherein $R^4$ has the above-mentioned meaning and X is fluoride, chloride, bromide, iodide or methanesulfonate.

Preferably $R^4$ is benzene-1,4-diyl; benzene-1,3-diyl; biphenyl-4,4'-diyl or oxydibenzene-4,1-diyl; and X is chloride, bromide or iodide.

It is also preferable using in the reaction approximately double molar amount of tetrahydro[1,3]oxazolo[2,3-b][1,3]oxazole of formula (7).

The Process for preparation of the new tris{4-methyltetrahydro[1,3]oxazolo[2,3-b][1,3]oxazol-4-ium} derivatives of general formula (5) is shown in scheme 5.

scheme 5

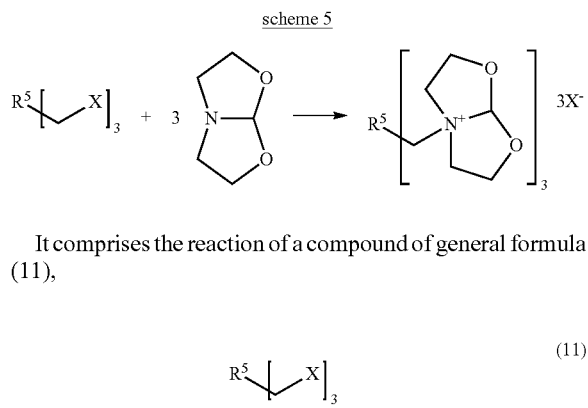

It comprises the reaction of a compound of general formula (11), (11)

with tetrahydro[1,3]oxazolo[2,3-b][1,3]oxazole of formula (7), wherein $R^5$ has the above-mentioned meaning and X is fluoride, chloride, bromide, iodide or methanesulfonate.

Preferably $R^5$ is benzene-1,3,5-triyl and X is chloride, bromide or iodide.

It is also preferable using in the reaction approximately triple molar amount of tetrahydro[1,3]oxazolo[2,3-b][1,3]oxazole of formula (7).

The skills required for carrying out the reaction and purification of the resulting products are known to those persons skilled in the art. The reaction is carried out in an organic solvent at a temperature of room temperature to the boiling point of reaction mixture, but no higher than 120° C., for a time period of 10 min. to 7 days, preferably at temperature no higher than 70° C., for a time period of 30 min. to 3 days. The solvent used in the synthesis is selected from alcohols; ethers; chlorinated hydrocarbons; N,N-dialkylamides; sulfoxides; aromatic hydrocarbons; ketones; esters; nitriles and mixtures thereof, preferably selected from methanol; ethanol; n-propanol; isopropanol; dichloromethane; chloroform; diethyl ether; diisopropyl ether; tetrahydrofurane; benzene; toluene; acetonitrile; N,N-dimethylformamide; dimethyl sulfoxide; ethyl acetate and mixtures thereof.

After reaction, the solvent is removed by evaporation or filtration and then, resulting crude product is purified by recrystallization from a solvent selected from alcohols; ketones; nitriles and mixtures thereof, preferably selected from methanol; ethanol; isopropanol; acetonitrile and mixtures thereof, in particular selected from ethanol or isopropanol.

In the context of the invention and unless otherwise mentioned in the text, the term "alkyl" denotes a monovalent linear or branched, saturated or unsaturated hydrocarbon group of 1 to 12 carbon atoms, preferably of 1 to 6 carbon atoms, for example, methyl, ethyl, propyl, isopropyl, n-butyl, iso-butyl, sec-butyl, tert-butyl.

The term "cycloalkyl" denotes a monovalent saturated or partially unsaturated mono- or bicyclic hydrocarbon group of 3 to 10 ring carbon atoms, preferably a monovalent saturated monocyclic hydrocarbon group of 3 to 8 ring carbon atoms, for example, cyclopropyl, cyclobutanyl, cyclopentyl, cyclohexyl, cycloheptyl, bicyclo[2.2.1]heptanyl, bicyclo[2.2.2]octanyl.

The term "aryl" denotes a monovalent aromatic carbocyclic mono- bi- or tricyclic ring system comprising 6 to 14 carbon ring atoms, for example, phenyl, naphthyl, anthracenyl.

The term "heteroaryl" denotes a monovalent aromatic heterocyclic mono-, bi- or tricyclic ring system of 5 to 16 ring atoms, comprising 1, 2, 3 or 4 heteroatoms selected from N, O and S, the remaining ring atoms being carbon, wherein secondary nitrogen atom is substituted with alkyl, acyl or aryl as mentioned herein. Examples of heteroaryl group include 1-methylpyrrolyl, furanyl, thienyl, 1-ethylimidazolyl, oxazolyl, thiazolyl, triazolyl, oxadiazolyl, thiadiazolyl, 1-phenyltetrazolyl, pyridinyl, pyrazinyl, 1-acetylpyrazolyl, pyridazinyl, pyrimidinyl, triazinyl, azepinyl, 1-methyldiazepinyl, isoxazolyl, benzofuranyl, isothiazolyl, benzothienyl, 1-phenylindolyl, isoindolyl, isobenzofuranyl, 1-formylbenzimidazolyl, benzoxazolyl, benzothiazolyl, benzooxadiazolyl, benzothiadiazolyl, 1-propylbenzotriazolyl, 9-benzylpurinyl, quinolinyl, isoquinolinyl, quinazolinyl, quinoxalinyl.

The term "amino" denotes a —$NH_2$ group.

The term "alkoxyl" denotes a group of the formula —O-Alk, wherein Alk is an alkyl group, for example, methoxyl, ethoxyl, n-propoxyl, isopropoxyl, n-butoxyl, isobutoxyl, tert-butoxyl.

The term "aryloxyl" denotes a group of the formula —O—Ar, wherein Ar is aryl, for example, phenoxyl, naphthoxyl.

The term "acyl" denotes groups of the formula —C(O)H, —C(O)-Alk or —C(O)—Ar, wherein Alk is alkyl and Ar is aryl, for example, formyl, acetyl, propionyl, butyryl, benzoyl.

The term "alkoxycarbonyl" denotes groups of the formula —O—C(O)—H or —O—C(O)-Alk, wherein Alk is alkyl, for example, formyloxidanyl, acetyloxidanyl, iso-propanoyloxidanyl.

The term "aryloxycarbonyl" denotes a group of the formula —O—C(O)—Ar, wherein Ar is aryl, for example, (phenylcarbonyl)oxidanyl, (naphthylcarbonyl)oxidanyl.

The term "halogen" denotes fluoro, chloro, bromo, or iodo.

The term "cyano" denotes a —C≡N group.

The term "alkylthio" denotes a group of the formula —S-Alk, wherein Alk is alkyl, for example, methylsulfanyl, ethylsulfanyl, propylsulfanyl, iso-propylsulfanyl.

The term "arylthio" denotes a group of the formula —S—Ar, wherein Ar is aryl, for example, phenylsulfanyl, naphthylsulfanyl.

The term "alkylsulfonyl" denotes a group of the formula —SO$_2$-Alk, wherein Alk is alkyl, for example, methylsulfonyl, ethylsulfonyl, propylsulfonyl, butylsulfonyl.

The term "arylsulfonyl" denotes a group of the formula —SO$_2$—Ar, wherein Ar is aryl, for example, phenylsulfonyl, naphthylsulfonyl.

The term "aminosulfonyl" denotes a —SO$_2$NH$_2$ group.

The term "nitro" denotes a —NO$_2$ group.

The term "room temperature" denotes a temperature ranging between 15 and 25° C.

In the third aspect, the present invention provides applications of the novel class of quaternary ammonium salts containing tetrahydro[1,3]oxazolo[2,3-b][1,3]oxazol-4-ium moiety. The application relates to the new derivatives of general formula (1) or (2) or (3) or (4) or (5), wherein:

$R^1$ or $R^3$ or $R^5$ is non-substituted or substituted group selected from alkyl, cycloalkyl, aryl or heteroaryl, wherein substituted group denotes group substituted with radical independently selected from alkyl, aryl, acyl, alkoxyl, aryloxyl, alkoxycarbonyl, aryloxycarbonyl, halogen, cyano, alkylthio, arylthio, alkylsulfonyl, arylsulfonyl, aminosulfonyl, nitro, amino, mono- or dialkylamino, mono- or diarylamino or acylamino;

$R^2$ or $R^4$ is non-substituted or substituted group selected from alkyl, cycloalkyl, aryl, heteroaryl, amino, mono- or dialkylamino, mono- or diarylamino or acylamino, wherein substituted group denotes group substituted with radical independently selected from alkyl, aryl, acyl, alkoxyl, aryloxyl, alkoxycarbonyl, aryloxycarbonyl, halogen, cyano, alkylthio, arylthio, alkylsulfonyl, arylsulfonyl, aminosulfonyl, nitro, amino, mono- or dialkylamino, mono- or diarylamino or acylamino;

X is fluoride, chloride, bromide, iodide or methanesulfonate;

as a cleaning agents, antistatics, foam-makers, emulsifiers, softeners, moisturizers or stabilisers used for the production of detergents, creams, shampoos, balms, shaving foams, hair dyes or regenerating conditioners.

The application relates also to the new derivatives of general formula (1) or (2) or (3) or (4) or (5), wherein:

$R^1$ or $R^2$ or $R^4$ or $R^3$ or $R^5$ and X have the above-mentioned meaning, as a germicides, fungicides, parasiticides, virucides, spermicides, disinfectants or antiseptics used for the production of washing, preserving or sterilizing agents or disinfectants.

The application relates also to the new derivatives of general formula (1) or (2) or (3) or (4) or (5), wherein:

$R^1$ or $R^2$ or $R^4$ or $R^3$ or $R^5$ and X have the above-mentioned meaning, as a phase transfer catalysts.

FIG. 1—presents the general structures of the new quaternary ammonium salts containing tetrahydro[1,3]oxazolo[2,3-b][1,3]oxazol-4-ium moiety.

The following examples are given for the purpose of illustrating the present disclosure and should not be considered as limitation on the scope or spirit of the disclosure.

$^1$H and $^{13}$C-NMR spectra were recorded on a Varian Unity 300 and Bruker Avance III 500 spectrometers at ambient temperature and in d$_6$-DMSO as a solvent. The chemical shifts δ are reported in ppm relative to tetramethylsilane (TMS) as a internal standard. The diffraction data were collected on an Agilent Xcalibur Atlas diffractometer, equipped with molybdenum lamp as a source of radiation. CrysAlisPro software was used for data collection and initial processing, Sir92 program was used to solve the structure and SHELXL-97 for the structure refinement.

EXAMPLE 1

4-benzyltetrahydro[1,3]oxazolo[2,3-b][1,3]oxazol-4-ium bromide

A solution of 1.710 g (10 mmol) of benzyl bromide and 1.152 g (10 mmol) of tetrahydro-[1,3]oxazolo[2,3-b][1,3]oxazole in 20 ml of diisopropyl ether was stirred at the room temperature for 24 hours. The precipitate was filtered off, washed twice with diisopropyl ether and dried. 2.698 g (94.3%) of white amorphous product was obtained, which can be further purified by recrystallisation from rectified ethanol.

$^1$H NMR (500 MHz, DMSO) δ 7.83 (d, J=7.0 Hz, 2H), 7.49 (dq, J=14.3, 7.1 Hz, 3H), 6.98 (s, 1H), 5.04 (s, 2H), 4.48-4.31 (m, 4H), 4.13 (dt, J=11.7, 7.5 Hz, 2H), 3.91 (dt, J=11.2, 5.7 Hz, 2H). $^{13}$C NMR (126 MHz, DMSO) δ 132.28, 130.33, 128.98, 128.72, 119.02, 66.83, 62.41, 57.35.

TABLE 1

| The crystallographic data and structure parameters | |
|---|---|
| Empirical formula | C$_{12}$H$_{16}$BrNO$_2$ |
| Formula weight | 285.16 |
| Temperature | 293(2) K |
| Wave length | 0.71073 Å |
| Crystal system, space group | monoclinic, P2(1)/n |
| Unit cell dimensions | a = 7.7184(2) Å    α = 90° |
| | b = 10.2120(3) Å   β = 99.816(3)° |
| | c = 15.6318(6) Å   γ = 90° |
| Volume | 1214.07(7) Å$^3$ |
| Z, calculated density | 4, 1.560 g/cm$^3$ |
| Absorption coefficient | 3.371 mm$^{-1}$ |
| F(000) | 580 |
| Crystal size | 1.0 × 0.4 × 0.2 mm |
| Theta range for data collection | 2.39 to 24.99° |
| Reflections collected/unique | 7773/2128 [R(int) = 0.0210] |
| Data/restraints/parameters | 2128/0/210 |
| Goodnes-of-fit | 0.986 |
| Extinction coefficient | 0.0062(7) |

EXAMPLE 2

4-(2-amino-2-oxoethyl)tetrahydro[1,3]oxazolo[2,3-b][1,3]oxazol-4-ium iodide

A solution of 1.850 g (10 mmol) iodoacetamide and 1.152 g (10 mmol) tetrahydro[1,3]oxazolo[2,3-b][1,3]oxazole in 20 ml of methanol was refluxed for 1 hour. The solvent was then removed under reduced pressure and the residue was allowed to crystallize overnight. The precipitate was filtered off, washed twice with dichloromethane and dried. 2.041 g (68.0%) of white crystalline product was obtained.

$^1$H NMR (500 MHz, DMSO) δ 7.82 (d, J=118.2 Hz, 2H), 6.65 (s, 1H), 4.46-4.33 (m, 6H), 4.13 (dt, J=11.5, 5.7 Hz, 2H), 3.88 (dt, J=12.1, 7.4 Hz, 2H). $^{13}$C NMR (126 MHz, DMSO) δ 165.19, 120.08, 66.73, 60.87, 60.31.

EXAMPLE 3

4-[2-(4-bromophenyl)-2-oxoethyl]tetrahydro[1,3]oxazolo[2,3-b][1,3]oxazol-4-ium bromide A solution of 2.779 g (10 mmol) 2,4'-dibromoacetophenone and 1.152 g (10 mmol) tetrahydro[1,3]oxazolo[2,3-b][1,3]oxazole in 20 ml of dichloromethane was refluxed for 3 hours. The precipitate was filtered off, washed twice with dichloromethane and dried. 3.801 g (96.7%) of white amorphous product was obtained, which can be further purified by recrystallisation from rectified ethanol.

$^1$H NMR (300 MHz, DMSO) δ 7.93 (d, J=8.7 Hz, 2H), 7.84 (d, J=8.6 Hz, 2H), 6.92 (s, 1H), 5.70 (s, 2H), 4.56-4.38 (m, 4H), 4.26 (dt, J=11.4, 5.7 Hz, 2H), 3.99 (dt, J=11.9, 7.1 Hz, 2H). $^{13}$C NMR (75 MHz, DMSO) δ 190.37, 133.00, 131.95, 130.03, 128.66, 120.87, 66.98, 66.28, 60.22.

EXAMPLE 4

4-[2-(biphenyl-4-yl)-2-oxoethyl]tetrahydro[1,3]oxazolo[2,3-b][1,3]oxazol-4-ium bromide A solution of 2.751 g (10 mmol) 2-bromo-4'-phenylacetophenone and 1.152 g (10 mmol) tetrahydro[1,3]oxazolo[2,3-b][1,3]oxazole in 20 ml of isopropanol was refluxed for 30 minutes. The reaction mixture was allowed to cool overnight and the precipitate was then filtered off, washed twice with dichloromethane and dried. 3.520 g (90.2%) of white fine crystalline product was obtained.

$^1$H NMR (400 MHz, DMSO) δ 8.08 (d, J=8.5 Hz, 2H), 7.95 (d, J=8.5 Hz, 2H), 7.84-7.77 (m, 2H), 7.57-7.41 (m, 3H), 6.92 (s, 1H), 5.70 (s, 2H), 4.55-4.41 (m, 4H), 4.28 (dt, J=11.5, 5.8 Hz, 2H), 4.00 (dt, J=11.9, 7.1 Hz, 2H). $^{13}$C NMR (101 MHz, DMSO) δ 190.58, 145.75, 138.42, 132.76, 129.15, 128.86, 128.75, 127.08, 126.96, 120.95, 67.00, 66.31, 60.35.

EXAMPLE 5

4-(4-nitrobenzyl)tetrahydro[1,3]oxazolo[2,3-b][1,3]oxazol-4-ium chloride

A solution of 1.716 g (10 mmol) 4-nitrobenzyl chloride and 1.152 g (10 mmol) tetrahydro-[1,3]oxazolo[2,3-b][1,3]oxazole in 20 ml of chloroform was stirred at the room temperature for 3 days. The precipitate was filtered off, washed twice with dichloromethane and dried. 2.161 g (75.4%) of white amorphous product was obtained, which can be further purified by recrystallisation from rectified ethanol.

$^1$H NMR (300 MHz, DMSO) δ 8.33 (d, J=8.7 Hz, 2H), 8.13 (d, =8.7 Hz, 2H), 6.98 (s, 1H), 5.14 (s, 2H), 4.46-4.36 (m, 4H), 4.12 (dt, J=11.7, 7.5 Hz, 2H), 3.97-3.85 (m, 2H). $^{13}$C NMR (75 MHz, DMSO) δ 148.57, 135.77, 133.85, 123.88, 119.55, 67.01, 61.12, 57.70.

EXAMPLE 6

4-(3-nitrobenzyl)tetrahydro[1,3]oxazolo[2,3-b][1,3]oxazol-4-ium chloride

A solution of 1.716 g (10 mmol) 3-nitrobenzyl chloride and 1.152 g (10 mmol) tetrahydro-[1,3]oxazolo[2,3-b][1,3]oxazole in 20 ml of chloroform was stirred at the room temperature for 3 days. The precipitate was filtered off, washed twice with dichloromethane and dried. 1.894 g (66.1%) of white amorphous product was obtained, which can be further purified by recrystallisation from rectified ethanol.

$^1$H NMR (300 MHz, DMSO) δ 8.74 (t, J=1.8 Hz, 1H), 8.38 (ddd, J=8.3, 2.2, 0.8 Hz, 1H), 8.31 (d, J=7.8 Hz, 1H), 7.82 (t, J=8.0 Hz, 1H), 7.00 (s, 1H), 5.14 (s, 2H), 4.40 (dd, J=7.5, 5.5 Hz, 4H), 4.14 (dt, J=11.7, 7.6 Hz, 2H), 3.95-3.79 (m, 2H). $^{13}$C NMR (75 MHz, DMSO) δ 148.06, 138.90, 130.80, 130.65, 127.25, 125.17, 119.51, 66.96, 61.17, 57.55.

EXAMPLE 7

Antimicrobial Activity of the New Quaternary Ammonium Salts

The four reference strains were indications of the minimum inhibitory concentration (MIC) and minimum bactericidal concentration (MBC) tests conducted for two newly synthesized compounds of the new quaternary ammonium salts derivatives: 4-[2-(4-bromophenyl)-2-oxoethyl]tetrahydro[1,3]oxazolo[2,3-b][1,3]oxazol-4-ium bromide and 4-[2-(biphenyl-4-yl)-2-oxoethyl]tetrahydro[1,3]oxazolo[2,3-b][1,3]oxazol-4-ium bromide. The study was carried out on strains: *Staphylocoocus aureus* ATCC 6538, *Escherichia coli* ATCC 25922, *Pseudomonas aeruginosa* ATCC 6749, *Candida albicans* ATCC 10231,

TABLE 2

Antimicrobial activity of analyzed compounds presented as MIC and MBC [g/l].

| | 4-[2-(4-bromophenyl)-2-oxoethyl]-tetrahydro[1,3]-oxazolo[2,3-b][1,3]-oxazol-4-ium bromide | | 4-[2-(biphenyl-4-yl)-2-oxoethyl]-tetrahydro[1,3]-oxazolo[2,3-b]-[1,3]oxazol-4-ium bromide | |
|---|---|---|---|---|
| Tested strain | MIC | MBC | MIC | MBC |
| *Staphylocoocus aureus* ATCC 6538 | (—) | 1.73 | (—) | 0.43 |
| *Escherichia coli* ATCC 25922 | (—) | 6.94 | (—) | 3.47 |
| *Pseudomonas aeruginosa* ATCC 6749 | 27.75 | 27.75 | 13.87 | 55.5 |
| *Candida albicans* ATCC 10231 | (—) | 27.75 | (—) | 6.94 |

The invention claimed is:
1. 4-Methyltetrahydro[1,3]oxazolo[2,3-b][1,3]oxazol-4-ium derivatives of the general formula (1),

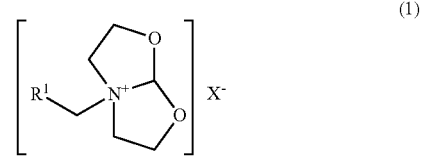

(1)

wherein:
R$^1$ is phenyl; 2-nitrophenyl; 3-nitrophenyl; 4-nitrophenyl; 2-bromophenyl; 3-bromophenyl; 4-bromophenyl; 2,3- dibromophenyl; 2,4-dibromophenyl; 2-chlorophenyl; 3-chlorophenyl; 4-chlorophenyl; 2,4-dichlorophenyl; 3,4-dichlorophenyl; 3,5-dichlorophenyl; 2,6-dichlorophenyl; 2-iodophenyl; 4-iodophenyl; 2-methoxyphenyl; 3-methoxyphenyl; 4-methoxyphenyl; 2,5-dimethoxyphenyl; 3,4-dimethoxyphenyl; 2,3,4-trimethoxyphenyl; 3,4,5-trimethoxyphenyl; 2-methylphenyl; 3-methylphenyl; 4-methylphenyl; 3,5-dimethylphenyl; 2,4-dimethylphenyl; 2-fluorophenyl; 3-fluorophenyl; 4-fluorophenyl; 3,4-difluorophenyl; 2,3-difluorophenyl; 3,5-difluorophenyl; 2,4-difluorophenyl; 2,3,4,5-tetrafluorophenyl; 2-(methoxycarbonyl)phenyl; 3-(methoxycarbonyl)phenyl; 4-(methoxycarbonyl)phenyl; 2-(trifluoromethyl)phenyl; 3-(trifluoromethyl)phenyl; 4-(trifluoromethyl)phenyl; 4-tert-butylphenyl; 2-phenylophenyl; 3-phenylophenyl; 4-phenylophenyl; 4-benzoylphenyl; 4-benzyloxyphenyl; 4-(methylsulphonyl)phenyl; 2-cyanophenyl; 3-cyanophenyl; 4-cyanophenyl; 4-formylphenyl; 4-methylthiophenyl; 3-phenoxyphenyl; 4-phenoxyphenyl; 2,4-diphenoxyphenyl; 2,4-dinitrophenyl; 4-(aminosulfonyl)phenyl; 2-pyridyl; 3-pyridyl; 4-pyridyl; 2-furyl; 2-thienyl; 2-benzo[b]furyl; 1-naphthyl or 2-naphthyl;

X is chloride, bromide or iodide, or bis{4-methyltetrahydro[1,3]oxazolo[2,3-b][1,3]oxazol-4-ium} derivatives of the general formula (3),

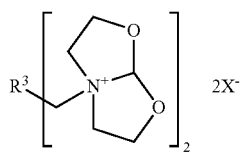

(3)

wherein:

$R^3$ is benzene-1,4-diyl; benzene-1,3-diyl; 1,2-dioxoethan-1,2-diyl; biphenyl-4,4'-diyl; methanediyldibenzene-4,1-diyl; oxodibenzene-4,1-diyl or carbonyldibenzene-4,1-diyl;

X is chloride, bromide or iodide, or tris{4-methyltetrahydro[1,3]oxazolo[2,3-b][1,3]oxazol-4-ium} derivatives of the general formula (5),

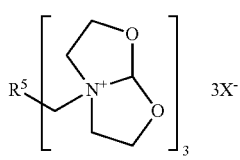

(5)

wherein:

$R^5$ is benzene-1,3,5-triyl;

X is chloride, bromide or iodide.

2. 4-(2-Oxoethyl)tetrahydro[1,3]oxazolo[2,3-b][1,3]oxazol-4-ium derivatives of the general formula (2),

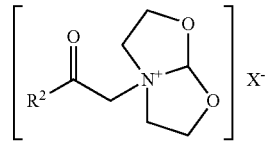

(2)

wherein:

$R^2$ is phenyl; 2-fluorophenyl; 3-fluorophenyl; 4-fluorophenyl; 2,4-difluorophenyl; 2,5-difluorophenyl; 2,6-difluorophenyl; 2,3,4-trichlorophenyl; 2,3,4,5-tetrafluorophenyl; 2-chlorophenyl; 3-chlorophenyl; 4-chlorophenyl; 2,4-dichlorophenyl; 3,4-dichlorophenyl; 2,5-dichlorophenyl; 2-bromophenyl; 3-bromophenyl; 4-bromophenyl; 3-iodophenyl; 4-iodophenyl; 2-hydroxyphenyl; 3-hydroxyphenyl; 4-hydroxyphenyl; 2,4-dihydroxyphenyl; 2,3-dihydroxyphenyl; 3,4-dihydroxyphenyl; 2,5-dihydroxyphenyl; 2-(acetyloxy)phenyl; 3-(acetyloxy)phenyl; 4-(acetyloxy)phenyl; 2,4-bis(acetyloxy)phenyl; 3,4-bis(acetyloxy)phenyl; 2,5-bis(acetyloxy)phenyl; 1,3-benzodioxol-5-yl; 2-phenylophenyl; 3-phenylophenyl; 4-phenylophenyl; 2-nitrophenyl; 3-nitrophenyl; 4-nitrophenyl; 2,4-dinitrophenyl; 3,4-dinitrophenyl; 2,5-dinitrophenyl; 4-chloro-3-nitrophenyl; 2-chloro-3-nitrophenyl; 2-methylphenyl; 3-methylphenyl; 4-methylphenyl; 2,4-dimethylphenyl; 3,4-dimethylphenyl; 2-methoxyphenyl; 3-methoxyphenyl; 4-methoxyphenyl; 3,4-dimethoxyphenyl; 2,4-dimethoxyphenyl; 2,5-dimethoxyphenyl; 3,4,5-trimethoxyphenyl; 4-ethylphenyl; 3-benzyloxyphenyl; 4-benzyloxyphenyl; 4-phenoxyphenyl; 2-cyanophenyl; 3-cyanophenyl; 4-cyanophenyl; 2-aminophenyl; 3-aminophenyl; 4-aminophenyl; 3-(trifluoromethyl)phenyl; 4-(trifluoromethyl)phenyl; 4-carbamoylphenyl; 4-sulfamoylphenyl; 4-(methylsulfonyl)phenyl; 4-(methoxycarbonyl)phenyl; 4-(acetylamino)phenyl; 4-(N,N-dimethylamino)phenyl; 4-tert-bu-.tylphenyl; trifluoromethyl; trichloromethyl; 2-pyridyl; 3-pyridyl; 4-pyridyl; 1-naphthyl; 2-naphthyl; 2-furyl; 2-benzo[b]furyl; 2-thienyl; amino; methylamino; dimethylamino; phenylamino; diphenylamino; benzylamino or dibenzylamino;

X is chloride, bromide or iodide, or bis{4-(2-oxoethyl)tetrahydro[1,3]oxazolo[2,3-b][1,3]oxazol-4-ium} derivatives of general formula (4),

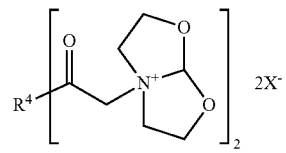

(4)

wherein:

$R^4$ is benzene-1,4-diyl; benzene-1,3-diyl; biphenyl-4,4'-diyl or oxydibenzene-4,1-diyl;

X is chloride, bromide or iodide.

3. The process for the preparation of 4-methyltetrahydro[1,3]oxazolo[2,3-b][1,3]oxazol-4-ium derivatives of general formula (1) of claim 1,

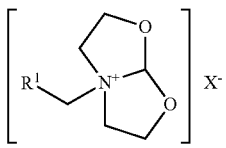

(1)

comprising the reaction of a compound of general formula (6),

(6)

with tetrahydro[1,3]oxazolo[2,3-ti][1,3]oxazole of formula (7),

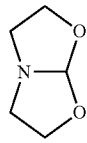

(7)

wherein:
R¹ is non-substituted or substituted group selected from alkyl, cycloalkyl, aryl, or heteroaryl, wherein substituted group denotes group substituted with radical independently selected from alkyl, aryl, acyl, alkoxyl, aryloxyl, alkoxycarbonyl, aryloxycarbonyl, halogen, cyano, alkylthio, arylthio, alkylsulfonyl, arylsulfonyl, amino-sulfonyl, nitro, amino, mono- or dialkylamino, mono- or diarylamino or acylamino;
X is fluoride, chloride, bromide, iodide or methanesulfonate.

4. The process according to claim 3, wherein:
R¹ is phenyl; 2-nitrophenyl; 3-nitrophenyl; 4-nitrophenyl; 2-bromophenyl; 3-bromophenyl; 4-bromophenyl; 2,3-dibromophenyl; 2,4-dibromophenyl; 2-chlorophenyl; 3-chlorophenyl; 4-chlorophenyl; 2,4-dichlorophenyl; 3,4-dichlorophenyl; 3,5-di-chlorophenyl; 2,6-dichlorophenyl; 2-iodophenyl; 4-iodophenyl; 2-methoxyphenyl; 3-methoxyphenyl; 4-methoxyphenyl; 2,5-dimethoxyphenyl; 3,4-dimethoxyphenyl; 2,3,4-trimethoxyphenyl; 3,4,5-trimethoxyphenyl; 2-methylphenyl; 3-methylphenyl; 4-methylphenyl; 3,5-dimethylphenyl; 2,4-dimethylphenyl; 2-fluorophenyl; 3-fluorophenyl; 4-fluorophenyl; 3,4-difluorophenyl; 2,3-difluorophenyl; 3,5-difluorophenyl; 2,4-difluorophenyl; 2,3,4,5-tetrafluorophenyl; 2-(methoxycarbonyl)phenyl; 3-(me-thoxycarbonyl)phenyl; 4-(methoxycarbonyl)phenyl; 2-(trifluoromethyl)phenyl; 3-(trifluoromethyl)phenyl; 4-(trifluoromethyl)phenyl; 4-tert-butylphenyl; 2-phenylophenyl; 3-phenylophenyl; 4-phenylophenyl; 4-benzoylphenyl; 4-benzyloxyphenyl; 4-(methylsulphonyl)phenyl; 2-cyanophenyl; 3-cyanophenyl; 4-cyanophenyl; 4-formylphenyl; 4-methylthiophenyl; 3-phenoxyphenyl; 4-phenoxyphenyl; 2,4-diphenoxyphenyl; 2,4-dinitrophenyl; 4-(aminosulfonyl)phenyl; 2-pyridyl; 3-pyridyl; 4-pyridyl; 2-furyl; 2-thienyl; 2-benzo[b]furyl; 1-naphthyl or 2-naphthyl;
X is chloride, bromide or iodide.

5. The process for the preparation of 4-(2-oxoethyl)tetrahydro[1,3]oxazolo[2,3-ti][1,3]oxa-zol-4-ium derivatives of general formula (2) of claim 2,

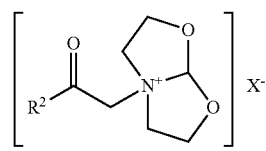

(2)

comprising the reaction of a compound of general formula (8),

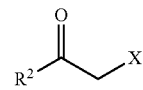

(8)

with tetrahydro[1,3]oxazolo[2,3-6][1,3]oxazole of formula (7),

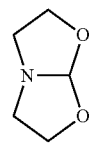

(7)

wherein:
R² is non-substituted or substituted group selected from alkyl, cycloalkyl, aryl, heteroaryl, amino, mono- or dialkylamino, mono- or diarylamino or acylamino, wherein substituted group denotes group substituted with radical independently selected from alkyl, aryl, acyl, alkoxyl, aryloxyl, alkoxycarbonyl, aryloxycarbonyl, halogen, cyano, alkylthio, arylthio, alkylsulfonyl, arylsulfonyl, aminosulfonyl, nitro, amino, mono- or dialkylamino, mono- or diarylamino or acylamino;
X is fluoride, chloride, bromide, iodide or methanesulfonate.

6. The process according to claim 5, wherein:
R² is phenyl; 2-fluorophenyl; 3-fluorophenyl; 4-fluorophenyl; 2,4-difluorophenyl; 2,5-difluorophenyl; 2,6-difluorophenyl; 2,3,4-trichlorophenyl; 2,3,4,5-tetrafluorophenyl; 2-chlorophenyl; 3-chlorophenyl; 4-chlorophenyl; 2,4-dichlorophenyl; 3,4-dichlorophenyl; 2,5-dichlorophenyl; 2-bromophenyl; 3-bromophenyl; 4-bromophenyl; 3-iodophenyl; 4-iodophenyl; 2-hydroxyphenyl; 3-hydroxyphenyl; 4-hydroxyphenyl; 2.4-dihydroxyphenyl; 2,3-dihydroxyphenyl; 3,4-dihydroxyphenyl; 2,5-dihydroxyphenyl; 2-(acetyloxy)phenyl; 3-(acetyloxy)phenyl; 4-(acetyloxy)phenyl; 2,4-bis(acetyloxy)phenyl; 3,4-bis(acetyloxy)phenyl; 2,5-bis(acetyloxy)phenyl; 1,3-benzodioxol-5-yl; 2-phenylophenyl; 3-phenylophenyl; 4-phenylophenyl; 2-nitrophenyl; 3-nitrophenyl; 4-nitrophenyl; 2,4-dinitrophenyl; 3,4-dinitrophenyl; 2,5-dinitrophenyl; 4-chloro-3-nitrophenyl; 2-chloro-3-nitrophenyl; 2-methylphenyl; 3-methylphenyl; 4-methylphenyl; 2,4-dimethylphenyl; 3,4-dimethylphenyl; 2-methoxyphenyl; 3-methoxyphenyl; 4-methoxyphenyl; 3,4-dimethoxyphenyl; 2,4-dimethoxyphenyl; 2.5-dimethoxyphenyl; 3,4,5-trimethoxyphenyl; 4-ethylphenyl; 3-benzyloxyphenyl; 4-benzyloxyphenyl; 4-phenoxyphenyl; 2-cyanophenyl; 3-cyanophenyl; 4-cyanophenyl; 2-aminophenyl; 3-aminophenyl; 4-aminophenyl; 3-(trifluoromethyl)phenyl; 4-(trifluoromethyl)phenyl; 4-carbamoylphenyl; 4-sulfamoylphenyl; 4-(methylsulfonyl)phenyl; 4-(methoxycarbonyl)phenyl; 4-(acetylamino)phenyl; 4-(N,N-dimethylamino)phenyl; 4-tert-butylphenyl; trifluoromethyl; trichloromethyl; 2-pyridyl; 3-pyridyl; 4-pyridyl; 1-naphthyl; 2-naphthyl; 2-furyl; 2-benzo[b]furyl; 2-thienyl; amino; methylamino; dimethylamino; phenylamino; diphenylamino; benzylamino or dibenzylamino;

X is chloride, bromide or iodide.

7. The process for the preparation of bis{4-methyltetrahydro[1,3]oxazolo[2,3-b][1,3]oxazol-4-ium} derivatives of general formula (3) of claim 1,

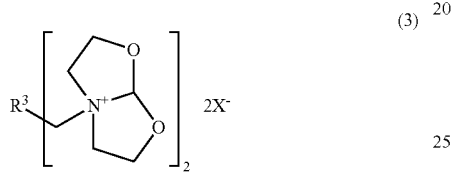

(3)

comprising the reaction of a compound of general formula (9),

(9)

with tetrahydro[1,3]oxazolo[2,3-b][1,3]oxazole of formula (7),

(7)

wherein:

$R^3$ is non-substituted or substituted group selected from alkyl, cycloalkyl, aryl or heteroaryl, wherein substituted group denotes group substituted with radical independently selected from alkyl, aryl, acyl, alkoxyl, aryloxyl, alkoxycarbonyl, aryloxycarbonyl, halogen, cyano, alkylthio, arylthio, alkylsulfonyl, arylsulfonyl, amino-sulfonyl, nitro, amino, mono- or dialkylamino, mono- or diarylamino or acylamino;

X is fluoride, chloride, bromide, iodide or methanesulfonate.

8. The process according to claim 7, wherein:

$R^3$ is benzene-1,4-diyl; benzene-1,3-diyl; 1,2-dioxoethan-1,2-diyl; biphenyl-4,4'-diyl; methanediyldibenzene-4,1-diyl; oxodibenzene-4,1-diyl or carbonyldibenzene-4,1-diyl;

X is chloride, bromide or iodide.

9. The process for the preparation of bis{4-(2-oxoethyl)tetrahydro[1,3]oxazolo[2,3-b][1,3]-oxazol-4-ium} derivatives of general formula (4) of claim 2,

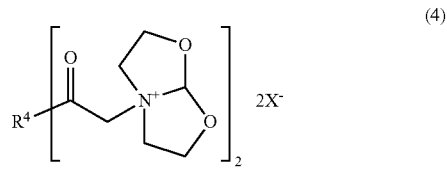

(4)

comprising the reaction of a compound of general formula (10),

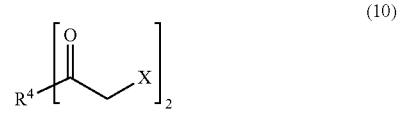

(10)

with tetrahydro[1,3]oxazolo[2,3-b][1,3]oxazole of formula (7),

(7)

wherein:

$R^4$ is non-substituted or substituted group selected from alkyl, cycloalkyl, aryl, heteroaryl, amino, mono- or dialkylamino, mono- or diarylamino or acylamino, wherein substituted group denotes group substituted with radical independently selected from alkyl, aryl, acyl, alkoxyl, aryloxyl, alkoxycarbonyl, aryloxycarbonyl, halogen, cyano, alkylthio, arylthio, alkylsulfonyl, arylsulfonyl, aminosulfonyl, nitro, amino, mono- or dialkylamino, mono- or diarylamino or acylamino;

X is fluoride, chloride, bromide, iodide or methanesulfonate.

10. The process according to claim 9, wherein:

$R^4$ is benzene-1,4-diyl; benzene-1,3-diyl; biphenyl-4,4'-diyl or oxydibenzene-4,1-diyl;

X is chloride, bromide or iodide.

11. The process for the preparation of tris{4-methyltetrahydro[1,3]oxazolo[2,3-6][1,3]oxazol-4-ium} derivatives of general formula (5) of claim 1,

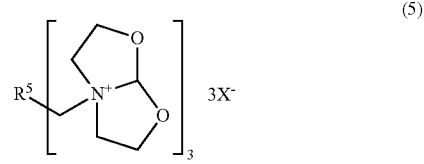

(5)

comprising the reaction of a compound of general formula (11),

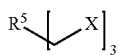
(11)

with tetrahydro[1,3]oxazolo[2,3-b][1,3]oxazole of formula (7),

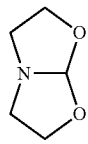
(7)

wherein:
$R^5$ is non-substituted or substituted group selected from alkyl, cycloalkyl, aryl or heteroaryl, wherein substituted group denotes group substituted with radical independently selected from alkyl, aryl, acyl, alkoxyl, aryloxyl, alkoxycarbonyl, aryloxycarbonyl, halogen, cyano, alkylthio, arylthio, alkylsulfonyl, arylsulfonyl, amino-sulfonyl, nitro, amino, mono- or dialkylamino, mono- or diarylamino or acylamino;
X is fluoride, chloride, bromide, iodide or methanesulfonate.

12. The process according to claim 11, wherein:
$R^3$ is benzene-1,3,5-triyl;
X is chloride, bromide or iodide.

13. The process according to claim 3, wherein the reaction is carried out using approximately equimolar amount of both reactants.

14. The process according to claim 7, wherein the reaction is carried out using approximately double molar amount of tetrahydro[1,3]oxazolo[2,3-b][1,3]oxazole with respect to compound of general formula (9).

15. The process according to claim 11, wherein the reaction is carried out using approximately triple molar amount of tetrahydro[1,3]oxazolo[2,3-b][1,3]oxazole with respect to compound of general formula (11).

16. The process according to claim 3, wherein the reaction is carried out in an organic solvent at a temperature of room temperature to the boiling point of reaction mixture, but no higher than 120° C., for a time period of 10 min. to 7 days.

17. The process according to claim 16, wherein reaction is carried out at a temperature no higher than 70° C., for a time period of 30 min. to 3 days.

18. The process according to claim 16, wherein the reaction is carried out in an organic solvent selected from alcohols; ethers; chlorinated hydrocarbons; N,N-dialkylamides; sulfoxides; aromatic hydrocarbons; ketones; esters; nitriles; and mixtures thereof.

19. The process according to claim 18, wherein the reaction is carried out in an organic solvent selected from methanol; ethanol; n-propanol; isopropanol; dichloromethane; chloroform; diethyl ether; diisopropyl ether; tetrahydrofurane; benzene; toluene; acetonitrile; N,N-dimethylformamide; dimethyl sulfoxide; ethyl acetate and mixtures thereof.

20. The process according to claim 16, wherein after reaction, the solvent is removed by evaporation or filtration and then, resulting crude product is purified by recrystallization from a solvent selected from the group consisting of methanol; ethanol; isopropanol; acetonitrile and mixtures thereof.

* * * * *